United States Patent
Jain

(10) Patent No.: US 11,083,728 B2
(45) Date of Patent: Aug. 10, 2021

(54) COMPOSITIONS OF CYCLIN DEPENDENT KINASE 7 (CDK7) INHIBITOR

(71) Applicant: Syros Pharmaceuticals, Inc., Cambridge, MA (US)

(72) Inventor: Neera Jain, Burlington, MA (US)

(73) Assignee: Syros Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 16/500,527

(22) PCT Filed: Apr. 3, 2018

(86) PCT No.: PCT/US2018/025934
§ 371 (c)(1),
(2) Date: Oct. 3, 2019

(87) PCT Pub. No.: WO2018/187357
PCT Pub. Date: Oct. 11, 2018

(65) Prior Publication Data
US 2020/0108067 A1    Apr. 9, 2020

Related U.S. Application Data

(60) Provisional application No. 62/483,127, filed on Apr. 7, 2017.

(51) Int. Cl.
*A61K 31/506* (2006.01)
*A61K 47/40* (2006.01)

(52) U.S. Cl.
CPC ............ *A61K 31/506* (2013.01); *A61K 47/40* (2013.01)

(58) Field of Classification Search
CPC .............................. A61K 31/506; A61K 47/40
USPC ........................................................ 514/275
See application file for complete search history.

(56) References Cited

U.S. PATENT DOCUMENTS 9,474,756 B2    10/2016    Horvath et al.
2016/0264551 A1    9/2016    Ciblat et al.

FOREIGN PATENT DOCUMENTS

WO    2015154038 A1    10/2015

OTHER PUBLICATIONS

Cancer [online], [retrieved on Jul. 6, 2007] Retrieved from the Internet, URL: http://www.nlm.nih.gov/medlineplus/cancer.html (Year: 2007).*
Lala et al., Role of nitric oxide in tumor progression: Lessons from experimental tumors, Cancer and Metastasis Reviews (1998), 17, 91-106 (Year: 1998).*
Golub et al., Molecular Classification of Cancer: Class Discovery and Class Prediction by Gene Expression Monitoring, Science (1999), vol. 286, 531-537 (Year: 1999).*
PubChem CID 10113978, create date Oct. 25, 2006.
Zhang et al. "Covalent targeting of remote cysteine residues to develop CDK12 and 13 inhibitors," Nat Chem Biol, 2016, 12(10):876-884.

* cited by examiner

*Primary Examiner* — Kristin A Vajda
(74) *Attorney, Agent, or Firm* — Goodwin Procter LLP

(57) ABSTRACT

The present invention provides, in part, compositions comprising an inhibitor of cyclin-dependent kinase 7 (CDK7) and sulfobutyl ether-β-cyclodextrin. Also provided are methods of using a disclosed composition for treating proliferative diseases. The present invention also provides methods of making disclosed compositions.

15 Claims, No Drawings

COMPOSITIONS OF CYCLIN DEPENDENT KINASE 7 (CDK7) INHIBITOR

CROSS-REFERENCE TO RELATED APPLICATIONS

This application is a U.S. National Phase Application under 35 U.S.C. § 371 of International Application No. PCT/US2018/025934, filed Apr. 3, 2018, which claims priority to and the benefit of U.S. Provisional Patent Application No. 62/483,127, filed Apr. 7, 2017, the entire contents of each of which are incorporated by reference herein in their entirety.

BACKGROUND OF THE INVENTION

CDK7 is ubiquitously expressed and plays a central role in the transcriptional machinery. CDK7 has been found associated with large regulatory regions called super-enhancers that define cell identity and cell state (Kwiatkowski et al., Nature Letter 616, Vol. 511 (2014).). In cancer, CDK7 is known to play a role in the transcription of oncogenic transcription factors, such as RUNX1 in T-cell acute lymphoblastic leukemia (Kwiatkowski et al.) and Myc in small cell lung cancer (Christiensen at al., Cancer Cell, 26, 909-922 (2014).) and neuroblastoma (Chipumuro et al., Cell, 159, 1126-1139 (2014).). In other diseases (e.g. inflammation) CDK7 inhibition has been shown to inhibit the NFkB pathway and reduce pro-inflammatory cytokines, cause neutrophil apoptosis to resolve established inflammation or suppress Th 17 cells and promote Treg ditferentiation to ameliorate experimental autoimmune disease. (Leitch A E, et al., Cell Death Differ. 2012; 19:1950-61; Yoshida H, et al., Biochem Biophys Res Commun. 2013; 435:378-84; Xia, Y et al., Clin Exp Med 2014; 15(3): 269-75. doi:10.1007/s10238-014-0305-6). Due to the ubiquitous nature of CDK7 and its responsibility for the transcription of key cellular genes, CDK7 inhibitors may be beneficial in treating other diseases including inflammatory disease, autoimmune conditions, infectious disease, etc.

SUMMARY OF THE INVENTION

The present invention relates to certain compositions comprising N-((1 S,3R)-3-(5-chloro-4-(1H-indol-3-yl)pyrimidin-2-ylamino)-1-methylcyclohexyl)-5-((E)-4-(dimethylamino)but-2-enamido)picolinamide (Compound 1), which is an inhibitor of CDK7 kinase activity, and uses thereof, for example, the prevention and/or treatment of proliferative diseases (e.g., cancers (e.g., leukemia, melanoma, multiple myeloma), benign neoplasms, angiogenesis, inflammatory diseases, autoinflammatory diseases, and autoimmune diseases) or infectious diseases in a subject. The compositions, in general, are formulated for parenteral use, or for reconstituting into a composition for parenteral use.

In one aspect, the present invention provides a pharmaceutical composition comprising a cyclodextrin (e.g., SBEβCD) and Compound 1.

In another aspect, the present invention provides a particulate composition comprising a cyclodextrin (e.g., SBEβCD) and Compound 1.

In another aspect, the present invention provides an aqueous solution comprising a cyclodextrin (e.g., SBEβCD) and Compound 1.

In another aspect, the present invention provides a pharmaceutical composition formulated for parental administration comprising a cyclodextrin (e.g., SBEβCD) and Compound 1.

Also provided in the present invention is a method of treating a subject suffering from a disease or condition associated with a gene or set of genes that are dependent upon CDK7 for transcription (a "CDK7-driven disease or condition"), comprising administering to the subject a disclosed composition or (e.g., a disclosed solution such as an aqueous solution described herein).

In one aspect, the present invention provides a method of preparing a disclosed particulate composition, wherein the method comprises: (a) dissolving a cyclodextrin (e.g., SBEβCD), Compound 1 or a pharmaceutically acceptable salt thereof, and optionally one or more pharmaceutically acceptable excipients in water; and (b) lyophilizing the solution.

In one aspect, the invention provides a method of preparing a solution, the method comprising dissolving a particulate composition (e.g., a lyophilized particulate composition) comprising a cyclodextrin (e.g., SBEβCD). Compound 1, and optionally one or more pharmaceutically acceptable excipients in an aqueous medium.

In still another aspect, the present invention provides methods of down-regulating a gene or set of genes that are dependent upon CDK7 for transcription in a subject.

Another aspect of the invention relates to methods of inhibiting the activity of a gene or set of genes that are dependent upon CDK7 for transcription in a subject.

The present invention also provides methods of inhibiting the growth of cells that require expression of a gene or set of genes that are dependent upon CDK7 for transcription in a subject.

In still another aspect, the present invention provides methods of inducing apoptosis of a cell whose survival requires expression of a gene or set of genes that are dependent upon CDK7 for transcription in a subject.

In still another aspect, the present invention provides methods of inhibiting other CDKs, specifically CDK12 and/or CDK13, with a composition described herein.

The details of one or more embodiments of the invention are set forth herein. Other features, objects, and advantages of the invention will be apparent from the Detailed Description, the Examples, and the Claims.

Definitions

The following definitions are more general terms used throughout the present application:

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other mammals (e.g., primates (e.g., cynomolgus monkeys, rhesus monkeys); commercially relevant mammals such as cattle, pigs, horses, sheep, goats, cats, and/or dogs). In certain embodiments, the subject is a human.

The terms "administer," "administering," or "administration," as used herein refers to parenteral administration, e.g., bolus injection or intravenous infusion.

As used herein, the terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, "treatment," "treat." and "treating" require that signs or symptoms of the disease disorder or condition have developed or have been observed. Treatment may also be continued after symptoms have resolved, for example, to delay or prevent recurrence.

As used herein, the terms "condition," "disease," and "disorder" are used interchangeably.

An "effective amount" of Compound 1 refers to an amount sufficient to elicit the desired biological response, i.e., treating the condition. As will be appreciated by those of ordinary skill in this art, the effective amount of Compound 1 may vary depending on such factors as the desired biological endpoint, the pharmacokinetics of the compound, the condition being treated, the mode of administration, and the age and health of the subject. An effective amount encompasses therapeutic and prophylactic treatment. For example, in treating cancer, an effective amount of an inventive composition of the invention may reduce the tumor burden or stop the growth or spread of a tumor.

A "therapeutically effective amount" of Compound 1 is an amount sufficient to provide a therapeutic benefit in the treatment of a condition or to delay or minimize one or more symptoms associated with the condition. In some embodiments, a therapeutically effective amount is an amount sufficient to provide a therapeutic benefit in the treatment of a condition or to minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of Compound 1 is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites.

As used herein, the term "CDK7-driven cancer" refers to a malignant neoplasmcharacterized by diseased cells that require the expression of a gene or set of genes that are dependent upon CDK7 for transcription. Exemplary CDK7-driven cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL. T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NI-IL) (e.g., B-cell NH L such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphomaileukemia, peripheral T-cell lymphoma (PTCL) (e.g., cutaneous T-cell lymphoma (CTCL) (e.g., mycosis fungoides, Sezary syndrome), angio-immunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic adenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

DETAILED DESCRIPTION OF CERTAIN EMBODIMENTS OF THE INVENTION

Compositions

The invention features compositions (e.g., pharmaceutical compositions) comprising Compound 1 and a cyclodextrin (e.g., SBEβCD), uses of these compositions, and methods of making these compositions. The compositions (e.g., pharmaceutical compositions) described herein include aqueous solutions as well as particulate compositions. For example, Compound 1 is dissolved in an aqueous solution with a cyclodextrin described herein such as SBEβCD. In some embodiments, the pH of the solution is adjusted with a buffer to help solubilize Compound 1. In some embodiments, additional excipients are included in the solution. The resulting aqueous solution is an example of a composition (e.g., an aqueous solution) of the invention. The aqueous solution can be lyophilized to create a particulate composition, which is another example of a composition of the invention. The particulate composition can be re-constituted, for example, at a hospital pharmacy. The re-constituted solution is an example of a composition of the invention. In embodiments, prior to administering Compound 1 to a subject, the re-constituted solution is diluted, for example, into an IV bag. This diluted composition is also a composition of the invention.

As used herein, Compound 1 refers to N-((1S,3R)-3-(5-chloro-4-(1H-indol-3-yl)pyrimidin-2-ylamino)-1-methylcyclohexyl)-5-((E)-4-(dimethylamino)but-2-enamido)picolinamide. The chemical structure of Compound 1 is represented by:

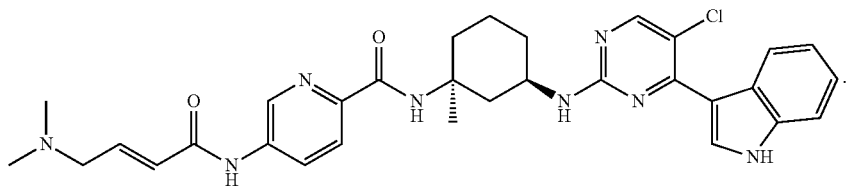 [SMILES: CN(C)C/C=C/C(=O)Nc1ccc(C(=O)N[C@@]2(C)CCC[C@@H](Nc3ncc(Cl)c(-c4c[nH]c5ccccc45)n3)C2)nc1]

Compound 1, as depicted above, denotes both specific stereochemistry of the substituents on the cyclohexyl moiety as well as specific configuration of the double bond. Compound 1, as used herein, is a substantially free of stereoisomers and configuration isomers not depicted in the structure above. In some embodiments, Compound 1, is at least about 95% pure (e.g., at least 95%, 97%, 98% or 98.5%, as depicted (e.g., less than 5%, 4%, 3%, 2%, or 1.5% of stereoisomers and conformational isomers not depicted). In some embodiments, an impurity in the composition is a degradation product of Compound 1, for example, a hydrolysis product of Compound 1, wherein the N(Me)₂ is replaced with an —OH. In some embodiments, this degradation product is about 1.2% by weight relative to Compound 1.

Compound 1, is a component in the compositions described herein. In some embodiments, when solubilizing Compound 1 into an aqueous solution, a buffer is used to adjust the pH of the aqueous solution (e.g., to improve the solubility of Compound 1 into the solution). In some embodiments, the pH of the resulting aqueous solution is from about 3 to about 7. In embodiments where the pH is below the pKa of Compound 1, Compound 1 can be in the form of a salt, or partially in the form of a salt. For example, when an aqueous solution having a pH less than the pKa of Compound 1 is lyophilized into a powder, the resulting powder will include a salt or partial salt of Compound 1. In some embodiments, the buffer in the aqueous solution is HCl. or phosphate, resulting in a chloride or phosphate salt or partial salt of Compound 1.

Compound 1 can exist as a tautomer. The term "tautomer" refers to a compound that has interchangeable forms, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane that are likewise formed by treatment with acid or base.

Cyclodextrins

Cyclodextrins are cyclic oligosaccharides containing or comprising six (α-cyclodextrin), seven (β-cyclodextrin), eight (γ-cyclodextrin), or more α-(1,4)-linked glucose residues. The hydroxyl groups of the cyclodextrins are oriented to the outside of the ring while the glucosidic oxygen and two rings of the non-exchangeable hydrogen atoms are directed towards the interior of the cavity. As a result, cyclodextrins possess a hydrophobic inner cavity combined with a hydrophilic exterior which conveys water solubility. Upon combination with a drug, such as Compound 1. (i.e., the guest) inserts into the hydrophobic interior of the cyclodextrin (i.e., the host). The host-guest complex retains water solubility as a consequence of the hydrophobic exterior of the cyclodextrin ring.

Compound 1 can be combined in a composition described herein with a cyclodextrin selected from the group consisting of α-cyclodextrin, β-cyclodextrin, γ-cyclodextrin, and derivatives thereof. The cyclodextrin may be chemically modified such that some or all of the primary or secondary hydroxyl groups of the macrocycle, or both, are functionalized with a pendant group. Suitable pendant groups include, but are not limited to, sulfinyl, sulfonyl, phosphate, acyl, and $C_1$-$C_{12}$ alkyl groups optionally substituted with one or more (e.g., 1, 2, 3, or 4) hydroxy, carboxy, carbonyl, acyl, oxy, oxo; or a combination thereof. Methods of modifying these alcohol residues are known in the art, and many cyclodextrin derivatives are commercially available, including sulfo butyl ether β-cyclodextrins available under the trade name CAPTISOL® from Ligand Pharmaceuticals (La Jolla, Calif.).

Examples of suitable cyclodextrins for use include cyclodextrins disclosed in U.S. Pat. Nos. 5,874,418; 6,046,177; and 7,635,733, which are herein incorporated by reference. Other examples of suitable cyclodextrins include α-cyclodextrin; β-cyclodextrin; γ-cyclodextrin; methyl α-cyclodextrin; methyl β-cyclodextrin; methyl γ-cyclodextrin; ethyl β-cyclodextrin; butyl α-cyclodextrin; butyl β-cyclodextrin; butyl γ-cyclodextrin; pentyl γ-cyclodextrin; hydroxyethyl β-cyclodextrin; hydroxyethyl γ-cyclodextrin; 2-hydroxypropyl α-cyclodextrin; 2-hydroxypropyl β-cyclodextrin; 2-hydroxypropyl γ-cyclodextrin; 2-hydroxybutyl O-cyclodextrin; acetyl α-cyclodextrin; acetyl β-cyclodextrin; acetyl γ-cyclodextrin; propionyl β-cyclodextrin; butyryl β-cyclodextrin; succinyl α-cyclodextrin; succinyl β-cyclodextrin; succinyl γ-cyclodextrin; benzoyl β-cyclodextrin; palmityl β-cyclodextrin; toluenesulfonyl β-cyclodextrin; acetyl methyl β-cyclodextrin; acetyl butyl β-cyclodextrin; glucosyl α-cyclodextrin; glucosyl β-cyclodextrin; glucosyl γ-cyclodextrin; maltosyl α-cyclodextrin; maltosyl β-cyclodextrin; maltosyl γ-cyclodextrin; α-cyclodextrin carboxymethylether; 3-cyclodextrin carboxymethylether; γ-cyclodextrin carboxymethylether; carboxymethylethyl β-cyclodextrin; phosphate ester α-cyclodextrin; phosphate ester β-cyclodextrin; phosphate ester γ-cyclodextrin; 3-trimethylammonium-2-hydroxypropyl β-cyclodextrin; sulfobutyl ether β-cyclodextrin; carboxymethyl α-cyclodextrin; carboxymethyl β-cyclodextrin; carboxymethyl γ-cyclodextrin, and combinations thereof.

Preferred cyclodextrins include, but are not limited to, alkyl cyclodextrins, hydroxy alkyl cyclodextrins, such as hydroxy propyl β-cyclodextrin, carboxy alkyl cyclodextrins and sulfoalkyl ether cyclodextrins, such as sulfo butyl ether β-cyclodextrin.

In one embodiment, the cyclodextrin is a β-cyclodextrin functionalized with a plurality of sulfobutyl ether groups. Such a cyclodextrins is sold under the tradename CAPTISOL®.

CAPTISOL® is a polyanionic beta-cyclodextrin derivative with a sodium sulfonate salt separated from the lipophilic cavity by a butyl ether spacer group, or sulfobutylether (SBE). CAPTISOL® is not a single chemical species, but comprised of a multitude of polymeric structures of varying degrees of substitution and positional/regional isomers dictated and controlled to a uniform pattern by a patented manufacturing process consistently practiced and improved to control impurities.

CAPTISOL® contains six to seven sulfobutyl ether groups per cyclodextrin molecule. Because of the very low pKa of the sulfonic acid groups, CAPTISOL® carries multiple negative charges at physiologically compatible pH values. The four-carbon butyl chain coupled with repulsion of the end group negative charges allows for an "extension" of the cyclodextrin cavity. This often results in stronger binding to drug candidates than can be achieved using other modified cyclodextrins. It also provides a potential for ionic charge interactions between the cyclodextrin and a positively charged drug molecule. In addition, these derivatives impart exceptional solubility and parenteral safety to the molecule. Relative to beta-cyclodextrin, CAPTISOL® provides higher interaction characteristics and superior water solubility in excess of 100 grams/100 ml, a 50-fold improvement.

As used herein, SBEβCD refers to sulfobutyl ether-β-cyclodextrin. A sulfobutyl ether-β-cyclodextrin having an average degree of substitution of about from about 6 to about 8 (e.g., about seven) is currently marketed as Captisol® (CyDex Pharmaceuticals, Inc., Lenexa, Kans.). Captisol®, has the following chemical structure:

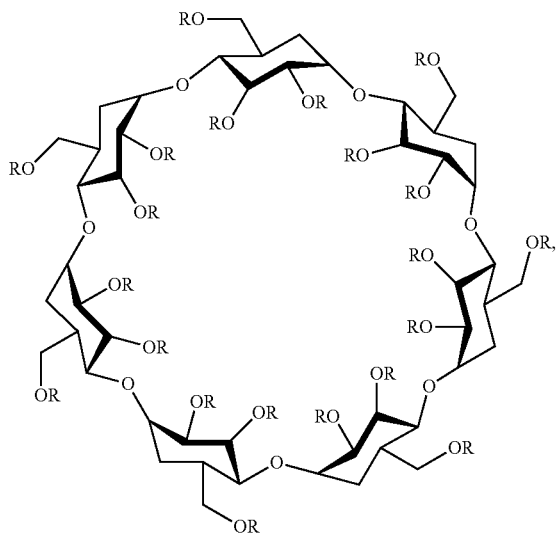

wherein R is $(-H)_{21-n}$ or $(-CH_2CH_2CH_2CH_2SO_3.Na^+)_n$, and n is 6-7.1.

In one aspect, the present invention provides a pharmaceutical composition comprising a cyclodextrin (e.g., SBEβCD) and Compound 1 or a pharmaceutically acceptable salt thereof.

In certain embodiments, the pharmaceutical composition comprising a cyclodextrin (e.g., SBEβCD) and Compound 1.

In certain embodiments, the pharmaceutical composition further comprises one or more pharmaceutically acceptable excipients. The term "pharmaceutically acceptable excipient" refers to a non-toxic carrier, adjuvant, diluent, or vehicle that does not destroy the pharmacological activity of the compound with which it is formulated. Pharmaceutically acceptable excipients useful in the manufacture of the pharmaceutical compositions of the invention are any of those that are well known in the art of pharmaceutical formulation and include inert diluents, dispersing and/or granulating agents, surface active agents and/or emulsifiers, disintegrating agents, binding agents, preservatives, buffering agents, lubricating agents, and/or oils. Pharmaceutically acceptable excipients useful in the manufacture of the pharmaceutical compositions of the invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

In certain embodiments, the pharmaceutical composition further comprises a surfactant.

In certain embodiments, the surfactant is a solutol, span, Tween (e.g., Tween 20 or Tween 80, or a povidone. In certain embodiments, the surfactant is a Tween such as Tween 80.

As noted above, in certain embodiments, Compound 1 is dissolved in an aqueous solution with a cyclodextrin described herein (e.g., SBEβCD). In some embodiments, the solution is a buffered solution, e.g., buffered with an acid.

In certain embodiments, the pharmaceutical composition further comprises an acid.

In certain embodiments, the acid is hydrochloric acid or phosphoric acid (e.g., hydrochloric acid).

In certain embodiments, the pH of the solution is from about 3 to about 4. In some embodiments, where the pH of the solution is from about 3 to about 4, Compound 1 has a concentration of from about 4 to about 6 mg/ml (e.g., about 5 mg/ml). In some embodiments, where the pH is from 3.5 to about 7 (e.g., from about 3.8 to about 5.5), Compound 1 has a concentration of from about 0.1 mg/ml to about 0.6 mg/ml. In some embodiments, compositions having a concentration of from about 0.1 mg/ml to about 0.6 mg/ml are pharmaceutical compositions administered to a subject.

In certain embodiments, SBEβCD has an average degree of substitution of about 6 to about 7.1.

In another aspect, the present invention provides a particulate composition comprising a cyclodextrin (e.g., SBEβCD) and Compound 1.

In certain embodiments, the weight-to-weight ratio of SBEβCD and Compound 1 is from about 30:1 to about 50:1.

In certain embodiments, the weight-to-weight ratio of SBEβCD and Compound 1 is about 40:1.

In certain embodiments, the particulate composition comprises from about 1% to about 3% by weight Compound 1.

In certain embodiments, the particulate composition further comprises one or more pharmaceutically acceptable excipients.

In certain embodiments, the particulate composition further comprises a surfactant.

In certain embodiments, the particulate composition comprises from about 1% and about 3% by weight surfactant.

In certain embodiments, the surfactant is a solutol, span, Tween (e.g., Tween 20 or Tween 80, or a povidone. In certain embodiments, the surfactant is a Tween such as Tween 80.

In certain embodiments, the particulate composition further comprises an acid (e.g., where the particulate composition is a lyophilite formed from lyophilization of an aqueous composition comprising Compound 1, a cyclodextrin and a buffer).

In certain embodiments, the acid is hydrochloric acid or phosphoric acid (e.g., hydrochloric acid).

In certain embodiments, the particulate is a lyophilizate.

In some embodiments, the particulate composition is stable, upon storage, for at least about 1 month (e.g., at least about 3 months, 6 months, or 9 months). In some embodiments, the particulate composition is stable, upon storage, for at least about 1 month under conditions of 5° C.±3° C., at 25° C.±2° C./60%±5% RH, or at 40° C.±2° C./75%±5% RH (e.g., for at least about 1 month (e.g., at least about 3 months, 6 months, or 9 months).

In one aspect, the present invention provides an aqueous solution comprising a cyclodextrin (e.g., SBEβCD) and Compound 1.

In certain embodiments, the weight-to-weight ratio of comprising a cyclodextrin (e.g., SBEβCD) and Compound 1 is from about 30:1 to about 50:1.

In certain embodiments, the weight-to-weight ratio of comprising a cyclodextrin (e.g., SBEβCD) and Compound 1 is about 40:1.

Compound 1 can be dissolved in an aqueous solution, such as a buffered aqueous solution. In some embodiments the solution is lyophilized into a particulate composition. The particulate composition can be dissolved (or re-dissolved) in an aqueous solution. In certain embodiments, the concentration of Compound 1 is from about 1 mg/mL to about 10 mg/mL, from about 2 mg/mL to about 8 mg/mL, or from about 4 mg/mL to about 6 mg/mL. In certain embodiments, the concentration of Compound 1 is about 5 mg/mL.

An aqueous solution described herein comprising Compound 1 and a cyclodextrin can be diluted, for example, injected into an bag (e.g., an IV bag) for administration to a subject. In certain embodiments, the concentration of Compound 1 (e.g., in a diluted solution described herein) is from about 0.1 mg/mL to about 1.0 mg/mL, from about 0.3 mg/mL to about 0.8 mg/mL, from about 0.5 mg/mL to about 0.7 mg/mL. In certain embodiments, the concentration of Compound 1 is from about 0.6 mg/mL. In certain embodiments, the concentration of Compound 1 is from about 0.005 mg/mL to about 0.05 mg/mL, from about 0.007 mg/ml, to about 0.03 mg/mL, or from about 0.009 mg/mL to about 0.02 mg/mL. In certain embodiments, the concentration of Compound 1 is about 0.01 mg/mL.

In certain embodiments, the aqueous solution further comprises one or more pharmaceutically acceptable excipients.

In certain embodiments, the aqueous solution further comprises a surfactant.

In certain embodiments, the surfactant is Tween 80.

In certain embodiments, the aqueous solution further comprises an acid.

In certain embodiments, the acid is hydrochloric acid.

In certain embodiments, the pH of the aqueous solution is from about 3.0 to about 4.0.

In one aspect, the present invention provides a pharmaceutical composition formulated for parental administration comprising SBEβCD and Compound 1 or a pharmaceutically acceptable salt thereof.

In certain embodiments, the pharmaceutical composition formulated for parental administration comprising SBEβCD and Compound 1.

In certain embodiments, the pharmaceutical composition further comprises one or more pharmaceutically acceptable excipients.

In certain embodiments, the composition (e.g., particulate or solution) comprises less than 100 ppm of a phosphate.

In certain embodiments, the composition (e.g., particulate or solution) comprises: less than 20 ppm of a sulfoalkylating agent; less than 0.5% by weight of an underivatized cyclodextrin; less than 1% by weight of an alkali metal halide salt; or less than 0.25% by weight of a hydrolyzed sulfoalkylating agent.

In certain embodiments, the composition (e.g., particulate or solution) comprises: less than 20 ppm of a sulfoalkylating agent; less than 0.5% by weight of an underivatized cyclodextrin; less than 1% by weight of an alkali metal halide salt; and less than 0.25% by weight of a hydrolyzed sulfoalkylating agent.

In certain embodiments, the composition (e.g., particulate or solution) comprises: less than 50 ppm of a phosphate; less than 10 ppm of a sulfoalkylating agent; less than 0.2% by weight of an underivatized cyclodextrin; less than 0.5% by weight of an alkali metal halide salt; or less than 0.1% by weight of a hydrolyzed sulfoalkylating agent.

In certain embodiments, the composition (e.g., particulate or solution) comprises: less than 50 ppm of a phosphate; less than 10 ppm of a sulfoalkylating agent; less than 0.2% by weight of an underivatized cyclodextrin; less than 0.5% by weight of an alkali metal halide salt; and less than 0.1% by weight of a hydrolyzed sulfoalkylating agent.

In certain embodiments, the composition (e.g., particulate or solution) comprises: less than 10 ppm of a phosphate; less than 2 ppm of a sulfoalkylating agent; less than 0.1% by weight of an underivatized cyclodextrin; less than 0.2% by weight of an alkali metal halide salt; or less than 0.08% by weight of a hydrolyzed sulfoalkylating agent.

In certain embodiments, the composition (e.g., particulate or solution) comprises: less than 10 ppm of a phosphate; less than 2 ppm of a sulfoalkylating agent; less than 0.1% by weight of an underivatized cyclodextrin; less than 0.2% by weight of an alkali metal halide salt; and less than 0.08% by weight of a hydrolyzed sulfoalkylating agent.

In certain embodiments, the composition (e.g., particulate or solution) comprises: less than 5 ppm of a phosphate less than 2 ppm of a sulfoalkylating agent; less than 0.1% by weight of an alkali metal halide salt; or less than 0.05% by weight of a hydrolyzed sulfoalkylating agent.

In certain embodiments, the composition (e.g., particulate or solution) comprises: less than 5 ppm of a phosphate; less than 2 ppm of a sulfoalkylating agent; less than 0.1% by weight of an alkali metal halide salt; and less than 0.05% by weight of a hydrolyzed sulfoalkylating agent.

In certain embodiments, the composition (e.g., particulate or solution) comprises: less than 250 ppb of a sulfoalkylating agent; less than about 0.1%, less than 0.08%, or less than 0.05% by weight of underivatized cyclodextrin; less than 200 ppm, less than 150 ppm, less than 100 ppm, less than 50 ppm, less than 20 ppm, less than 10 ppm, less than 5 ppm, or less than 2 ppm of a phosphate; less than 1%, less than 0.5%, less than 0.2%, less than 0.1%, less than 0.08%, or less than 0.05% by weight of alkali metal halide salt; or less than 1%, less than 0.5%, less than 0.2%, less than 0.1%, less than 0.08%, or less than 0.05% by weight of hydrolyzed sulfoalkylating agent.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Methods of Preparing a Composition

The present invention also provides a method of preparing a disclosed composition comprising: (a) dissolving SBEβCD, Compound 1, and optionally one or more pharmaceutically acceptable excipients in water; and (b) lyophilizing the solution.

In certain embodiments, the method further comprises adding an acid to the solution. In certain embodiments, the acid is hydrochloric acid.

In certain embodiments, the method further comprises measuring the pH of the solution.

In certain embodiments, the method further comprises adding an acid to the solution to adjust the pH of the solution. In certain embodiments, the targeted pH of the solution is from about 3.2 to about 4. In certain embodiments, the acid is hydrochloric acid.

In certain embodiments, the method further comprises filtering the solution.

In certain embodiments, the water is water for injection.

The present invention also provides a method of preparing a solution, the method comprising dissolving a particulate composition (e.g., a lyophilized particulate composition) comprising SBEβCD, Compound 1, and optionally one or more pharmaceutically acceptable excipients in an aqueous medium. In some embodiments, the composition is agitated, e.g., for at least 30 seconds, e.g., at least 60, 90, 120, 150, 180, 210, or 240 seconds.

Kits, and Administration

Compositions and pharmaceutical compositions described herein can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Compositions of the present invention may be administered parenterally. In some embodiments, provided compounds or compositions are administrable intravenously. The term "parenteral" as used herein includes subcutaneous, intravenous, intramuscular, intraocular, intravitreal, intraarticular, intra-synovial, intrasternal intrathecal, intrahepatic, intrapetitoneal intralesional and intracranial injection or infusion techniques. Sterile injectable forms of the compositions of this invention may be aqueous. Among the acceptable vehicles and solvents that may be employed are water, Ringer's solution, dextrose (e.g., 5% dextrose) and isotonic sodium chloride solution. In addition, sterile, fixed oils are conventionally employed as a solvent or suspending medium.

Although the descriptions of pharmaceutical compositions provided herein are principally directed to pharmaceutical compositions which are suitable for administration to humans, it will be understood by the skilled artisan that such compositions are generally suitable for administration to mammals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compositions provided herein are typically formulated in dosage unit form, e.g., single unit dosage form, for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment, drugs used in combination or coincidental with the specific active ingredient employed; and like factors well known in the medical arts.

The exact amount of a composition required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage is delivered using multiple administrations (e.g., two, three, four, five, six, seven, eight, nine, ten, eleven, twelve, thirteen, fourteen, or more administrations). In certain embodiments, the desired dosage is delivered two times a week.

In certain embodiments, Compound 1 may be at dosage levels sufficient to deliver from about 1 mg to about 100 mg, from about 5 mg to about 50 mg, from about 10 mg to about 40 mg, from about 15 mg to about 35 mg, from about 20 mg to about 30 mg, from about 22 mg to about 27 mg, about 25 mg, about 10 mg, about 15 mg, about 20 mg, about 30 mg, about 35 mg, about 40 mg, about 50 mg, about 75 mg, or about 100 mg to obtain the desired therapeutic effect. In a preferred embodiment, the dosage level is 25 mg of Compound 1.

In an embodiment, Compound 1 is dosed to a subject (e.g., a human subject) at an amount of from about 2 mg/m$^2$ to about 90 mg/m$^2$. For example, Compound 1 is dosed to a subject at an amount of from about 20 mg/m$^2$ to about 40 mg/m$^2$. In an embodiment, Compound 1 is dosed to a subject at about 2 mg/m$^2$. In an embodiment, Compound 1 is dosed to a subject at about 90 mg/m$^2$.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a composition, as described herein, can be administered in combination with one or more additional pharmaceutical agents. The compounds or compositions can be administered in combination with additional pharmaceutical agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The composition can be administered concurrently with, prior to, or subsequent to, one or more additional pharmaceutical agents, which may be useful as, e.g., combination therapies. Pharmaceutical agents include therapeutically active agents. Pharmaceutical agents also include prophylactically active agents. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the composition of the invention with the additional pharmaceutical agents and/or the desired therapeutic and/or prophylactic effect to be achieved. In general, it is expected that the additional pharmaceutical agents utilized in combination be utilized at levels that do not exceed the levels at which they are utilized individually. In some embodiments, the levels utilized in combination will be lower than those utilized individually.

Exemplary additional pharmaceutical agents include, but are not limited to, anti-proliferative agents, anti-cancer agents, anti-diabetic agents, anti-inflammatory agents, immunosuppressant agents, anti-emetic agents and a pain-relieving agent. Pharmaceutical agents include small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

Also encompassed by the invention are kits (e.g., pharmaceutical packs). The inventive kits may be useful for preventing and/or treating a proliferative disease (e.g., cancer (e.g., leukemia, melanoma, multiple myeloma), benign neoplasm, angiogenesis, inflammatory disease, autoinflammatory disease, or autoimmune disease). The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the container and the second container are combined to form one unit dosage form.

Thus, in one aspect, provided are kits including a first container comprising a composition described herein. In certain embodiments, the kit of the invention includes a first container comprising a composition described herein. In certain embodiments, the kits are useful in preventing and/or treating a proliferative disease in a subject. In certain embodiments, the kits further include instructions for administering the composition, to a subject to prevent and/or treat a proliferative disease.

Methods of Treatment and Uses

The present invention also provides methods for the treatment or prevention of a prolitferative disease (e.g., cancer, benign neoplasm, angiogenesis, inflammatory disease, autoinflammatory disease, or autoimmune disease) or an infectious disease (e.g., a viral disease) in a subject. Such methods comprise the step of administering to the subject in need thereof an effective amount of a composition described herein (e.g., a solution described herein). In certain embodiments, the methods described herein include administering to a subject an effective amount of a composition described herein.

In another aspect, the present invention provides a method of treating a subject suffering from a CDK7-dependent disease or condition, comprising administering to the subject a composition or a solution described herein.

In certain embodiments, the CDK7-dependent disease or condition is selected from the group consisting of cancer, benign neoplasm, angiogenesis, inflammatory disease, autoinflammatory disease, autoimmune disease, and an infectious disease.

In certain embodiments, the disease is CDK7-dependent cancer.

In certain embodiments, the CDK7-dependent cancer is selected from the group consisting of a blood cancer, melanoma, a bone cancer, a breast cancer, a brain cancer, and a lung cancer.

In certain embodiments, the CDK7-dependent cancer is selected from the group consisting of chronic lymphocytic leukemia (CLL), acute lymphoblastic leukemia (ALL), T cell acute lymphoblastic leukemia (T ALL), chronic myelogenous leukemia (CM L), acute myelogenous leukemia (AML), lymphoma, and multiple myeloma.

In certain embodiments, the CDK7-dependent cancer is selected from the group consisting of osteosarcoma, Ewing's sarcoma, chordoma, ovarian cancer, triple negative breast cancer (TNBC), neuroblastoma, and small cell lung cancer (SCLC).

In certain embodiments, the pharmaceutical composition or aqueous solution is administered parentally.

In certain embodiments, the method further comprises administering to the subject one or more additional agents independently selected from the group consisting of anti-proliferative agents, anti-cancer agents, immunosuppressant agents, and pain relieving agents.

In certain embodiments, the subject being treated is a mammal. In certain embodiments, the subject is a human.

In other embodiments, the CDK7-dependent proliferative disease to be treated or prevented using the compositions described herein will also be characterized by the expression of a gene or set of genes whose transcription is controlled by t CDK12 and/or CDK13. The compositions described herein, may also inhibit the transcription of such genes.

A proliferative disease may also be associated with inhibition of apoptosis of a cell in a subject. That inhibition may be driven by the product of a gene or a set of genes whose transcription is controlled by CDK7 (or CDK12 or CDK13). Inhibition of the activity of CDK7 is expected to cause cytotoxicity via reduced expression of such gene(s) allowing for induction of apoptosis. The compositions described herein, may induce apoptosis, and therefore, be useful in treating and/or preventing proliferative diseases.

In some embodiments, the CDK7-dependent proliferative disease is associated with angiogenesis. All types of angiogenesis disclosed herein or known in the art are contemplated as being within the scope of the invention.

In certain embodiments, the CDK7-dependent proliferative disease is an inflammatory disease. All types of inflammatory diseases disclosed herein or known in the art are contemplated as being within the scope of the invention. In certain embodiments, the inflammatory disease is rheumatoid arthritis. In some embodiments, the proliferative disease is an autoinflammatory disease. All types of autoinflammatory diseases disclosed herein or known in the art are contemplated as being within the scope of the invention. In some embodiments, the proliferative disease is an autoimmune disease. All types of autoimmune diseases disclosed herein or known in the art are contemplated as being within the scope of the invention.

The cell described herein may be an abnormal cell. In certain embodiments, the abnormal cell is a proliferative cell. In certain embodiments, the abnormal cell is a blood cell. In certain embodiments, the abnormal cell is a lymphocyte. In certain embodiments, the abnormal cell is a cancer cell. In certain embodiments, the abnormal cell is a leukemia cell. In certain embodiments, the abnormal cell is a CLL cell. In certain embodiments, the abnormal cell is a melanoma cell. In certain embodiments, the abnormal cell is a multiple myeloma cell. In certain embodiments, the abnormal cell is a benign neoplastic cell.

In other embodiments, the cell described herein is a normal cell whose activity is responsible for the disease or condition to be treated. For example, the cell may be responsible for recruiting inflammatory cells through the expression of genes whose transcription is controlled by CDK7. In certain embodiments, the normal cell is an endothelial cell. In certain embodiments, the normal cell is an immune cell.

In certain embodiments, the methods described herein comprise the additional step of administering one or more additional pharmaceutical agents in combination with a composition described herein. Such additional pharmaceutical agents include, but are not limited to, anti-proliferative agents, anti-cancer agents, anti-diabetic agents, anti-inflammatory agents, immunosuppressant agents, and a pain-relieving agent. The additional pharmaceutical agent(s) may synergistically augment inhibition of CDK7 or CDK12 and/or CDK13 induced by the inventive compositions of this invention in the biological sample or subject. Thus, the combination of the inventive compositions and the additional pharmaceutical agent(s) may be useful in treating proliferative diseases resistant to a treatment using the additional pharmaceutical agent(s) without the inventive compositions.

In yet another aspect, the present invention provides the compositions described herein, for use in the treatment of a proliferative disease in a subject. In certain embodiments provided by the invention are the compositions described herein, for use in the treatment of a proliferative disease in a subject. In certain embodiments, provided by the invention are the compositions described herein, for use in inhibiting cell growth. In certain embodiments, provided by the invention are the compositions described herein, for use in inducing apoptosis in a cell. In certain embodiments, provided by the invention are the compositions described herein, for use in inhibiting transcription.

EXAMPLES

In order that the invention described herein may be more fully understood, the following examples are set forth. The synthetic and biological examples described in this application are offered to illustrate the compounds, pharmaceucompositions, and methods provided herein and are not to be construed in any way as limiting their scope.

Example 1—Particulate Composition of Compound 1

A particulate composition containing Compound 1 was prepared as a freeze-dried powder in a clear glass vial fitted with a rubber stopper and seal containing 25 mg/vial of Compound 1, SBEβCD (1 g), Tween 80 (25 mg), and hydrochloric acid to adjust pH to 3.5.

TABLE 1

Composition of Compound 1

| Component | Grade | Function | Quantity/vial |
|---|---|---|---|
| Compound 1 | In-house | Active Ingredient | 25 mg[a] |
| Sulfoxybutyl Ether Cyclodextrin | In-house | Solubility enhancer | 1 g |
| Super Refined Tween 80 | USP/NF | Solubility enhancer | 25 mg |
| 1N Hydrochloric acid | USP/NF | to adjust pH | adjust pH to 3.5 |
| Water for Injection[b] | USP | Solvent | q.s. |

[a]Amount may be adjusted based upon drug substance purity;
[b]Water is removed during lyophilization.

At the time of dosing, each vial is to be reconstituted with 5 mL of water for injection, and then further diluted into normal saline for infusion via a central intravenous line over a 60-minute period.

Example 2—Manufacturing Method of Particulate Composition of Compound 1

The particulate composition of Compound 1 of Example 1 was prepared according to the procedure described below.

1N HCl solution was prepared from concentrated HCl. Approximately 70% of Water for Injection (WFI) was added to a clean compounding vessel. SBEβCD was added to the compounding vessel. The solution was mixed until the SBEβCD was dissolved. Super Refined Tween 80 was added to the compounding vessel and mixed until it dissolved. Compound 1 was added to the compounding vessel and mix. 1N HCl was added to the compounding vessel and the solution was mixed until complete dissolution of Compound 1. The clarity of the solution was visually confirmed and the pH of the solution was measured. The targeted range of the pH is from 3.2 to 4. If necessary, 1N HCl was added to adjust the pH. Water for Injection was added to make the concentration of Compound 1 reach 5 mg/mL. The final pH of the bulk solution was measured. A sample of the solution was tested for pre-filtration bioburden. Two 0.22 μm filters were used for sterile filtration of the solution. Pre- and post-filtration bubble point of the filters was measured. Washed and depyrogenated vials (20 mL) were filled with 5 mL of the compounded bulk and partially stoppered with washed and autoclaved stoppers. The solution in the vials was lyophilized. The vials were capped and sealed.

Example 3—Reconstituted and Infusion Solution Stability

The stability of the reconstituted solution of the particulate composition of Compound 1 of Example 1 was determined up to 4 hours. Duplicate vials of Compound 1 were reconstituted each with 5 mL of Water for Injection, USP. The stability test of the solution at initial and 4 hours following storage at room temperature and light showed a slight decrease in concentration of Compound 1 with no measurable change in impurities and unchanged appearance and pH.

TABLE 2

Stability data for Compound 1 reconstituted solution (5 mg/mL) (n = 2)

| Time Points (hours) | Initial | 4 hours |
|---|---|---|
| Appearance | Yellowish Clear solution | Yellowish Clear solution |
| pH | 3.2 | 3.2 |
| Compound 1 concentration (mg/mL) | 4.75 | 4.48 |
| Impurities (% a/a) | RRT 1.04 = 0.71% | RRT 1.04 = 0.70% |
| | RRT 1.23 = 0.10% | RRT 1.23 = 0.07% |
| | RRT 1.46 = 0.55% | RRT 1.44 = 0.59% |
| | RRT 1.48 = 0.48% | RRT 1.47 = 0.42% |
| | RRT 1.62 = 0.09% | RRT 1.61 = 0.09% |
| | Total = 1.9% | Total = 1.9% |

For the infusion solution stability study, duplicate dilutions of the reconstituted Compound 1 in 0.9% Sodium Chloride for Injection, LISP to provide the low (0.01 mg/mL) and high dose (0.6 mg/mL) were prepared. Infusion bags and sets used were made of polyolefin and polyethylene-lined respectively. To bracket the concentrations to be used in the clinic, two concentrations (0.01 mg/mL and 0.6 mg/mL of Compound 1) representing lowest and highest doses were selected. The stability of low and high dose infusion bag dilution is summarized in Table 3 and Table 4, respectively. In summary, the results showed no changes in concentration between the initial and after 4 hours of storage at ambient temperature and light at both low and high dose. Although an increase in pH was found for the low dose dilution, this did not result in decrease in the concentration of Compound 1.

TABLE 3

Stability data for Compound1 infusion solution at 0.01 mg/mL

| Time Paints (hours) | Initial | 4 hours |
|---|---|---|
| Appearance | Yellowish Clear solution | Yellowish Clear solution |
| pH | 7.6 | 8.1 |
| Compound 1 concentration (mg/mL) | 0.0096 | 0.0099 |
| Impurities (% a/a) | ND | ND |

ND—concentration too low to detect any measurable impurities

TABLE 4

Stability data for Compound 1 infusion solution at 0.6 mg/mL

| | Time Points (hours) | |
|---|---|---|
| | Initial | 4 hours |
| Appearance | Yellowish Clear Solution | Yellowish Clear Solution |
| pH | 3.6 | 3.6 |

TABLE 4-continued

Stability data for Compound 1 infusion solution at 0.6 mg/mL

| | Time Points (hours) | |
|---|---|---|
| | Initial | 4 hours |
| Compound 1 concentration (mg/mL) | 0.552 | 0.551 |
| Impurities (% a/a) | RRT 1.03 = 0.71% | RRT 1.03 = 0.71% |
| | RRT 1.22 = 0.06% | RRT 1.22 = 0.06% |
| | RRT = 1.43 = 0.51% | RRT = 1.43 = 0.51% |
| | RRT = 1.60 = 0.08% | RRT = 1.60 = 0.08% |
| | Total = 1.4% | Total = 1.4% |

Example 4—Formulation Development of Compound 1

The equilibrium solubility measurements in various pharmaceutical excipients were conducted and are listed in Table 5. The drug is poorly soluble in water, and can only be improved in acidic conditions (pH<4) due to protonation of the tertiary amine moiety. The co-solvents PEG 300 and PEG 400 show good solubility (>19 mg/mL) however the drug is unstable on long-term storage. Captisol®, on the other hand, shows good solubility especially when combined with acidic conditions (pH 3-4) and in combination with Tween 80. A lyophilized formulation was developed for a bulk solution containing 5 mg/mL SY-1365, 20% w/w Captisol®, 0.5% Tween 80, HCl to adjust pH to 3.5, and water.

TABLE 5

Equilibrium Solubility of Compound 1

| Aqueous Solvents | Solubility (mg/mL) |
|---|---|
| Water | 0.00012 |
| Sorensen phosphate Buffer | <LOQ |
| 50 mM KCl, pH 2 | 3.6 |
| 50 mM Citrate pH 4 | 0.0037 |
| 50 mM Phosphate pH 6 | 0.0019 |
| 50 mM Phosphate pH 8 | <LOQ |
| 50 mM Borate pH 10 | <LOQ |
| Dehydrated Alcohol | 3.6 |
| t-Butanol | 3.2 |
| Propylene Glycol | 4.0 |
| PEG 300 | >19.4 |
| PEG 400 | >20.8 |
| Tween 80 | 18.3 |
| 10% Captisol, pH 5.5 (phosphate buffer) | 4.6 |
| 20% Captisol, pH 5.5 (phosphate buffer) | 5.9 |
| 20% Captisol, 0.1% Tween 80, pH 3.5, (HCl) | >10 |

Example 5—Stability Study for Compound 1 25 mg/Vial Powder for Injection

Stability studies for Compound 1 Powder for Injection, 25 mg/vial are ongoing for two prototype development batches manufactured at Lyophilization Technology Inc (LTI), a development engineering batch and cGMP batch manufactured at Patheon Greenville (NC).

Clinical/GMP Batch (AG6102A) of SY-1365 Powder for Injection, 25 mg/Vial

Stability studies on cGMP Batch AG6102A will be tested according to the protocol in Table 6. The stability studies will be conducted for as long as they are relevant to assess the stability of clinical material, or until the planned end of the stability study. If a batch fails to conform to the stability specification at the long-term storage conditions, implications of the data will be evaluated for all affected clinical batches to ensure the identity, strength, purity, and quality of the clinical supplies. If necessary, supplies will be withdrawn from the clinic promptly.

TABLE 6

Compound 1 Powder for Injection, 25 mg/vial cGMP Batch Stability Study Design

| Storage condition | Stability time points (months) | | | | | | | |
|---|---|---|---|---|---|---|---|---|
| | 1 | 3 | 6 | 9 | 12 | 18 | 21 | 36 |
| 5° C. ± 3° C. | A | A | A | A | A, B | A | A, B | A, B |
| 25° ± 2° C./60% ± 5% RH | A | A | A | A | A, B | NR | NR | NR |
| 40° ± 2° C./75% ± 5% RH | A | NR | NR | NR | NR | NR | NR | NR |

Conclusions: Five and a half months stability data from development batch of Compound 1, 25 mg/vial Powder for injection formulation at long term condition of 2-8° C. and accelerated condition of 25° C./60% R.H and one month at 40° C./75% RH showed no visible trends or changes in appearance of lyophilized powder and reconstituted solution, pH, moisture, potency, related substances. These data, along with one month stability of other development batches and engineering batch with on-going cGMP stability studies, as well as drug substance stability support the proposed storage condition of 2-8° C., protect from light for Compound 1 Powder for Injection.

Equivalents and Scope

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior alt.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A pharmaceutical composition comprising SBEβCD and N-((1S,3R)-3-(5-chloro-4-(1H-indol-3-yl)pyrimidin-2-ylamino)-1-methylcyclohexyl)-5-((E)-4-(dimethylamino)but-2-enamido)picolinamide (Compound 1) or a pharmaceutically acceptable salt thereof.

2. The pharmaceutical composition of claim 1, wherein the composition further comprises one or more pharmaceutically acceptable excipients, a surfactant, or an acid.

3. The pharmaceutical composition of claim 2, wherein the surfactant is Tween 80 and the acid is hydrochloric acid.

4. The pharmaceutical composition of claim 1, wherein the SBEβCD has an average degree of substitution of about 6 to about 7.

5. The pharmaceutical composition of claim 1, wherein the composition is a particulate composition or an aqueous solution.

6. The pharmaceutical composition of claim 5, wherein the weight-to-weight ratio of the SBEβCD and Compound 1 or the pharmaceutically acceptable salt thereof is from about 30:1 to about 50:1.

7. The pharmaceutical composition of claim 5, wherein the composition is particulate and comprises from about 1% to about 3% by weight Compound 1, or the pharmaceutically acceptable salt thereof, or wherein the composition is an aqueous solution comprising 1 mg/mL to about 10 mg/mL Compound 1 or the pharmaceutically acceptable salt thereof.

8. The pharmaceutical composition of claim 5, wherein the composition is particulate and further comprises from about 1% to about 3% by weight surfactant.

9. The pharmaceutical composition of claim 1, wherein the composition comprises a therapeutically effective amount of Compound 1 or the pharmaceutically acceptable salt thereof.

10. The pharmaceutical composition of claim 5, wherein the particulate is a lyophilizate.

11. The pharmaceutical composition of claim 5, wherein the composition is an aqueous solution having a pH from about 3.0 to about 4.0.

12. The pharmaceutical composition of claim 5, wherein the composition further comprises less than 100 ppm of a phosphate.

13. The pharmaceutical composition of claim 5, wherein the composition further comprises:
    less than 20 ppm of a sulfoalkylating agent;
    less than 0.5% by weight of an underivatized cyclodextrin;
    less than 1% by weight of an alkali metal halide salt; or
    less than 0.25% by weight of a hydrolyzed sulfoalkylating agent.

14. The pharmaceutical composition of claim 1, wherein the composition is formulated for parenteral administration.

15. A method of preparing the pharmaceutical composition of claim 5, wherein the composition is a particulate and the method comprises:
    (a) dissolving SBEβCD, N-((1S,3R)-3-(5-chloro-4-(1H-indol-3-yl)pyrimidin-2-ylamino)-1-methylcyclohexyl)-5-((E)-4-(dimethylamino)but-2-enamido)picolinamide (Compound 1) or a pharmaceutically salt thereof, and optionally one or more pharmaceutically acceptable excipients in water; and
    (b) lyophilizing the solution.

\* \* \* \* \*